United States Patent
Summer et al.

(10) Patent No.: US 6,482,005 B1
(45) Date of Patent: Nov. 19, 2002

(54) METHOD AND APPARATUS FOR SHAPING DENTAL FILLING MATERIAL

(75) Inventors: John D. Summer, Portland, OR (US); Gregory B. Stock, Los Angeles, CA (US)

(73) Assignee: John Summer, Portland, OR (US)

( * ) Notice: Subject to any disclaimer, the term of this patent is extended or adjusted under 35 U.S.C. 154(b) by 0 days.

(21) Appl. No.: 09/465,413

(22) Filed: Dec. 16, 1999

(51) Int. Cl.[7] ............................................... A61C 5/04
(52) U.S. Cl. ........................................................ 433/39
(58) Field of Search .......................... 433/39, 136, 148, 433/155

(56) References Cited

U.S. PATENT DOCUMENTS

| | | | |
|---|---|---|---|
| 638,973 A | 12/1899 | Mehlig | 433/40 |
| 804,099 A | 11/1905 | Chase | 433/39 |
| 1,133,379 A * | 3/1915 | Hollingsworth | 433/39 |
| 1,265,581 A | 5/1918 | Zurbrigg | 433/39 |
| 1,794,213 A | 2/1931 | Spahn | 433/23 |
| 2,288,011 A | 6/1942 | Mizzy | 433/148 |
| 2,353,747 A * | 7/1944 | Morrison | 433/39 |
| 2,591,745 A | 4/1952 | Tofflemire | 433/155 |
| 2,607,117 A | 8/1952 | Baughan | 433/39 |
| 2,790,238 A | 4/1957 | Trangmar | 433/39 |
| 2,835,628 A | 5/1958 | Saffir | 433/39 |
| 3,074,169 A | 1/1963 | Freeman | 433/39 |
| 3,082,531 A | 3/1963 | Jacobsen | 433/39 |
| 3,145,472 A | 8/1964 | Tofflemire | 433/39 |
| 3,305,928 A | 2/1967 | Tofflemire | 433/39 |
| 3,421,222 A | 1/1969 | Newman | 433/39 |
| 3,842,505 A | 10/1974 | Eames | 433/39 |
| 4,024,643 A * | 5/1977 | Eisenberg | 433/39 |
| 4,373,915 A | 2/1983 | Comstock | 433/136 |
| 4,523,909 A | 6/1985 | Lazarus | 433/39 |
| 4,563,152 A | 1/1986 | McClure | 433/39 |
| 4,608,021 A | 8/1986 | Barrett | 433/229 |
| 4,704,087 A | 11/1987 | Dragan | 433/39 |
| 4,718,849 A | 1/1988 | von Wissenfluh et al. | 433/39 |
| 4,909,736 A * | 3/1990 | Ritter | 433/39 |
| 5,330,353 A | 7/1994 | Wavrin | 433/39 |
| 5,342,194 A | 8/1994 | Feldman | 433/39 |
| 5,380,198 A | 1/1995 | Suhonen | 433/39 |
| 5,505,618 A | 4/1996 | Summer | 433/148 |
| 5,586,883 A | 12/1996 | Nakisher et al. | 433/39 |
| 5,791,898 A | 8/1998 | Maissami | 433/164 |
| 5,899,694 A | 5/1999 | Summer | 433/136 |
| 5,951,801 A | 9/1999 | Weissenfluh et al. | 433/39 |
| 6,142,778 A * | 11/2000 | Summer | 433/39 |

FOREIGN PATENT DOCUMENTS

EP    0241107 A1    10/1987

OTHER PUBLICATIONS

*Sullivan–Schein Dental Catalogue*, pp. 313–314 (no publication date on these sheets).
*Dental Products*, "Matrix Bands" product description, Jul. 1998.
*Dental Products Report*, Light–Curing Matrix, Nov. 1999.

* cited by examiner

Primary Examiner—John J. Wilson
(74) Attorney, Agent, or Firm—Klarquist Sparkman LLP

(57) ABSTRACT

A flexible frame supports and at least partially surrounds a thin polymer sheet. The frame and polymer sheet is positioned between a tooth being filled and an adjacent tooth so as to extend partly or completely around the buccal and lingual sides of the tooth being filled. The frame may be severable to facilitate removal of the frame and apparatus following the completion of a filling. A mechanism may be included for tightening the gingival border of the frame to more closely follow the natural tooth contour. A mechanism may also be included for tightening the occlusal border of the frame with such tightening mechanisms being independently operated. The frame may be secured to a tooth being treated such as utilizing adhesive tabs.

21 Claims, 4 Drawing Sheets

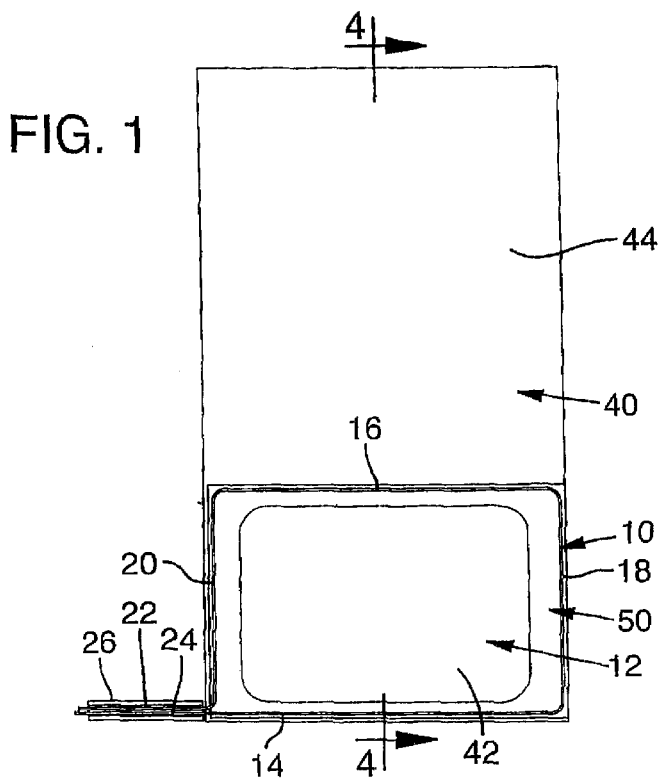
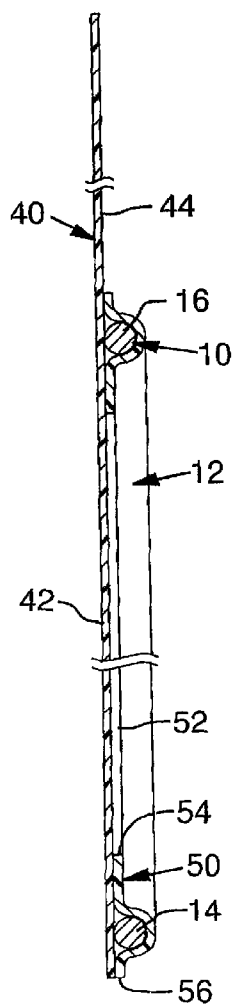
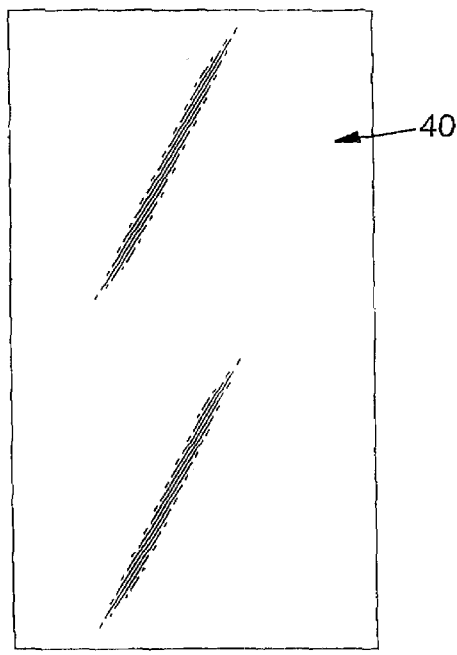
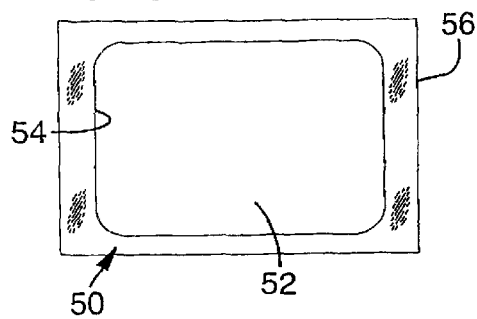

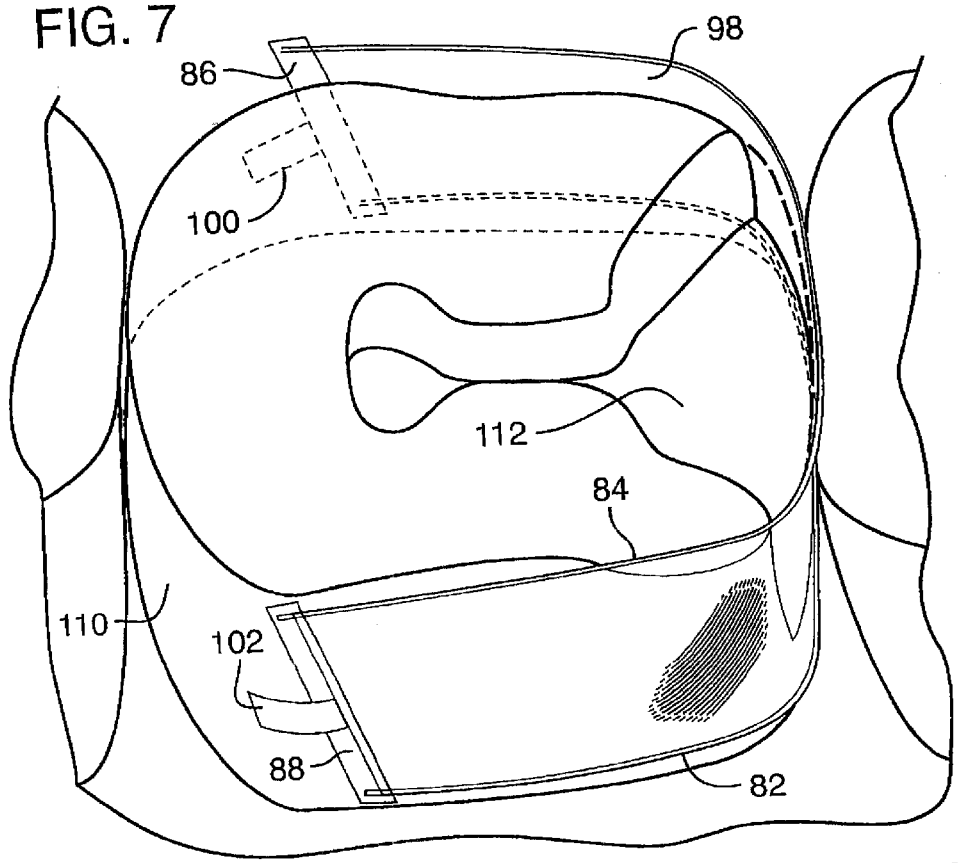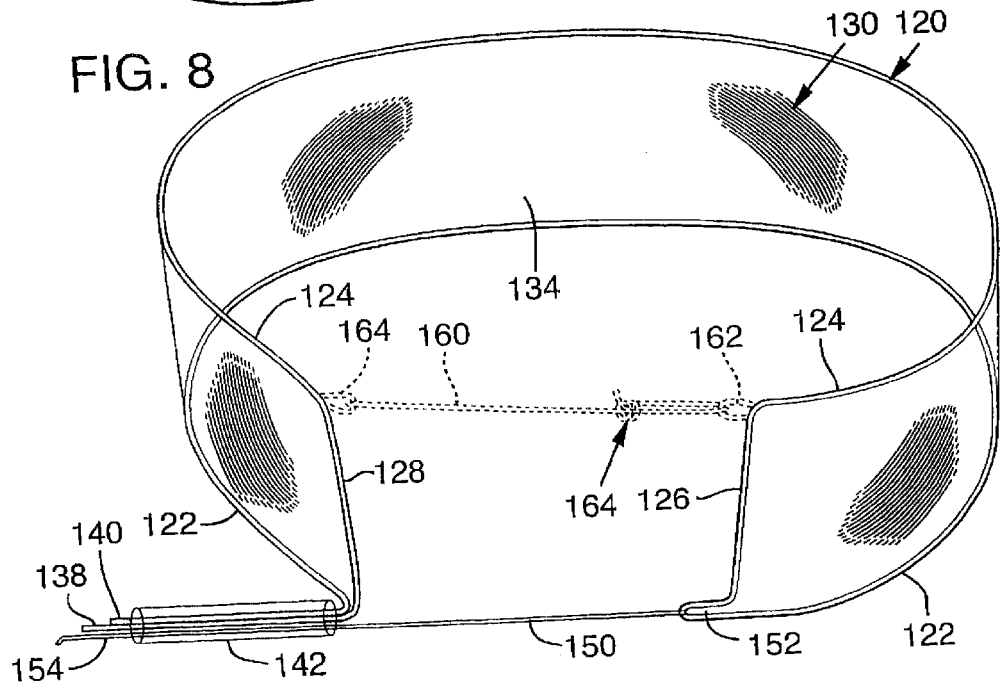

METHOD AND APPARATUS FOR SHAPING DENTAL FILLING MATERIAL

BACKGROUND

The present invention relates to devices and methods for shaping tooth filling material, such as composite resin, which has been placed in a tooth cavity preparation.

In dentistry, teeth which are subject to decay are typically drilled or otherwise prepared by removing the decayed tooth material. This leaves an aperture, slot or other void in the tooth which needs to be filled with composite resin or other filling material. When dentists fill class 2 cavity preparations, they typically insert a temporary substrate adjacent to the cavity preparation to contain and control the flow of filling material. The temporary substrate that dentists have traditionally used is an elongated band called a matrix band. The bands are typically placed in some type of a retaining device and then tightened around the prepared tooth by rotating a portion of the retaining device with the tightening being accomplished shortly before the filling process is begun. One example of a matrix band is found in U.S. Pat. No. 5,380,198 to Suhonen. This particular band has at least one window covered by a transparent strip of plastic such as cellulose acetate. The plastic strip rests against the dental filling material which may be cured using light. This patent also mentions retaining the matrix band in position with the aid of a matrix tightener such as used in a Tofflemire system.

One problem with conventional matrix band retaining devices is they are tightened by mechanical mechanisms which apply the force at a point midway between the gingival and occlusal border of the band. For example, such deviceds typically pinch the two ends of the band at a point midway between the gingival and occlusal border of the band and draw them through a slot (as in the Tofflemire matrix retainer) or wind the two ends around a rotating shaft (as in the Automatrix and other so-called spool retainers). Matrix bands are designed with a shape such that when they are placed in one of these retainers and tightened around a tooth with an average shape and taper, they will fit the tooth well. However when they are tightened around a tooth with a shape that tapers more than average, the bands do not fit the gingival margin well. Since adaptation of the matrix band at its gingival border is important to the success of the restoration, dentists often force wedges in between the teeth as close as possible to the gingiva in order to ensure good adaptation of the matrix band at the gingival border of the filling. Such wedge placement is time consuming and ineffective in enhancing adaptation on the buccal or lingual aspects of the interproximal area where there are no opposing surfaces to wedge against.

Another problem with conventional matrix band retainers is that, when they are used to tighten matrix bands around teeth, the force exerted is not resilient and is therefore difficult to control. The dentist typically applies force by turning a shaft until the shaft stops turning because the inner surface of the matrix band becomes tight against the outer circumference of the tooth at some point, preventing any further tightening. The dentist then simply stops turning the shaft and performs the filling, relying on the friction in the mechanism to prevent the shaft from turning slightly back and releasing the tension of the matrix band around the tooth. Some turning back of the mechanism may occur after the tightening has ceased.

Since most of the composite resins used to fill teeth today are light cured resins, clear plastic bands offer significant advantages over metal matrix bands. Composite resin can be observed by a dentist through the clear plastic band to ensure that there are no unfilled voids before curing. In addition, the composite resin may then be cured by shining light through the clear plastic band to ensure a better depth of cure. However, clear plastic matrix bands which are known to the inventors have been composed of strips of mylar (polyester) which is at least 0.0015 inch thick or plastic materials such as mentioned in U.S. Pat. No. 5,380,198. The materials in U.S. Pat. No. 5,380,198 are also understood to be relatively thick. This patent equates in one example, the thickness of the plastic to the thickness of a steel band included in the device of e.g., 0.05 mm thickness.

Therefore, there is a need for an improved apparatus and method for shaping tooth filling material. The present invention does not require the solution of all of the problems of the prior art. Instead, the invention is directed toward new and unobvious features and methods set forth in this disclosure both alone and in combination with one another and as set forth in the claims below.

SUMMARY

In accordance with one embodiment, it is desirable for a tooth filling material shaping apparatus to be thin, have a light transmissive section, and be flexible enough so that it will closely follow the natural tooth contours when tightened around a tooth. It is also desirable in accordance with this embodiment to utilize a tightening device which holds the band tight around the tooth by means of light elastic forces.

In accordance with another aspect of an embodiment, a sheet of very thin polymer material is attached to a frame which defines at least one frame opening. The sheet may be a polymer film. Preferably the thickness of the sheet material positioned between the proximal or adjacent most surfaces of two adjacent teeth during filling of one of the teeth is no more than 0.0006 inch and preferably from about 0.0003 inch to 0.0006 inch. A light transmissive material, such as clear polyethylene may be used. The frame, which may be coupled to the sheet in any suitable manner, such as using adhesive or heat sealing, holds the plastic sheet taut in the frame opening and is flexible enough so that it can be easily bent or wrapped around a tooth to be filled. When positioned and tightened around the tooth, the frame is preferably flexible enough to closely follow the natural unprepared contours of the tooth being filled. A mechanism may be included for tightening the frame with the preferred approach involving the application of a tensioning force to at least the gingival portion of the frame.

The frame may contain an area which is easily severed, such as by breaking or by detaching detachably coupled frame elements so that the frame may easily be removed after a filling is complete without requiring the gingival portion of the frame to be pushed upwardly between contacting proximal teeth surfaces during the removal process. For example, the frame may be formed by a wire, which may be multi-stranded, with at least one frame opening being defined by looping the wire with first and second ends of the wire projecting outwardly from the loop. These ends of the wire may be positioned adjacent to one another and detachably secured together, for example by inserting the wires through a sleeve. This sleeve may be heat shrunk to more securely hold the wires together. Following completion of the filling, the ends of the wires may be removed from the sleeve and separated. The portion of the wire extending along the gingiva between adjacent teeth may then be pulled laterally until it emerges from between the teeth to thereby facilitate removal of the apparatus from a patient's mouth. The frame may alternatively be cut or otherwise severed or broken to permit removal of the frame.

In accordance with an aspect of an embodiment, the frame may contain a mechanism which permits the dentist to fasten it to or hold it in position relative to a tooth being filled. Also, the frame is flexible such that the filling material shaping apparatus may be positioned and held in a wide variety of spatial relationships relative to the tooth to assist a dentist in achieving a desired contour when completing the filling. This increases the versatility of use of the device. As one specific example, the frame may include a mechanism which allows a dentist to tighten the gingival border of the frame around the tooth so as to enhance the close adaptation of the gingival margins of the completed filling so that the filling at such margins blends in smoothly with the remaining unprepared natural contours of the tooth. Close adaptation of the filling at the gingival margins is especially important because an overhang or an over-contoured area at the gingival margin may leave gingival tissues without sufficient functional stimuli to keep them healthy and may impair the ability of the patient to floss. The tightening mechanism may have some elasticity. Although desirable to tighten the apparatus by a tensioning force applied along the gingival border, and this may be the only location at which the tightening force is applied, it is also possible to tighten the apparatus by applying a biasing force at other locations such as the occlusal border.

The frame may also carry a section of sheet material which may be rolled, folded onto or otherwise positioned against the filling material on the biting surface of the tooth. This section may be unsupported and may comprise an occlusal extension section which can be positioned out of the dentist's way until the filling material has been placed. Following placing of the filling material, including on the occlusal or biting surface of the tooth, the occlusal extension may be positioned onto the occlusal surface over the filling material. The patient may then bite down on the occlusal extension to directly mold a new restored bite surface.

Additional features of embodiments of the present invention are set forth in the detailed description below and shown in the drawings. The invention includes novel and unobvious elements, acts, features and methods described herein both individually and collectively and is not limited to any specific exemplary embodiments or approaches.

BRIEF DESCRIPTION OF THE DRAWINGS

FIG. 1 is a front elevational view of a first embodiment of a dental filling material shaping apparatus including an optional occlusal extension.

FIG. 2 shows a single sheet of material used in the embodiment of FIG. 1.

FIG. 3 shows a second sheet of material having an opening therethrough which is combined in the embodiment of FIG. 1.

FIG. 4 shows a vertical section view taken along line 4—4 of FIG. 1.

FIG. 7 illustrates an embodiment of FIG. 6 shown in position on a tooth.

FIG. 8 illustrates an embodiment with one form of a mechanism for tightening the gingival edge of a frame included in the embodiment.

DETAILED DESCRIPTION

Figure 5:
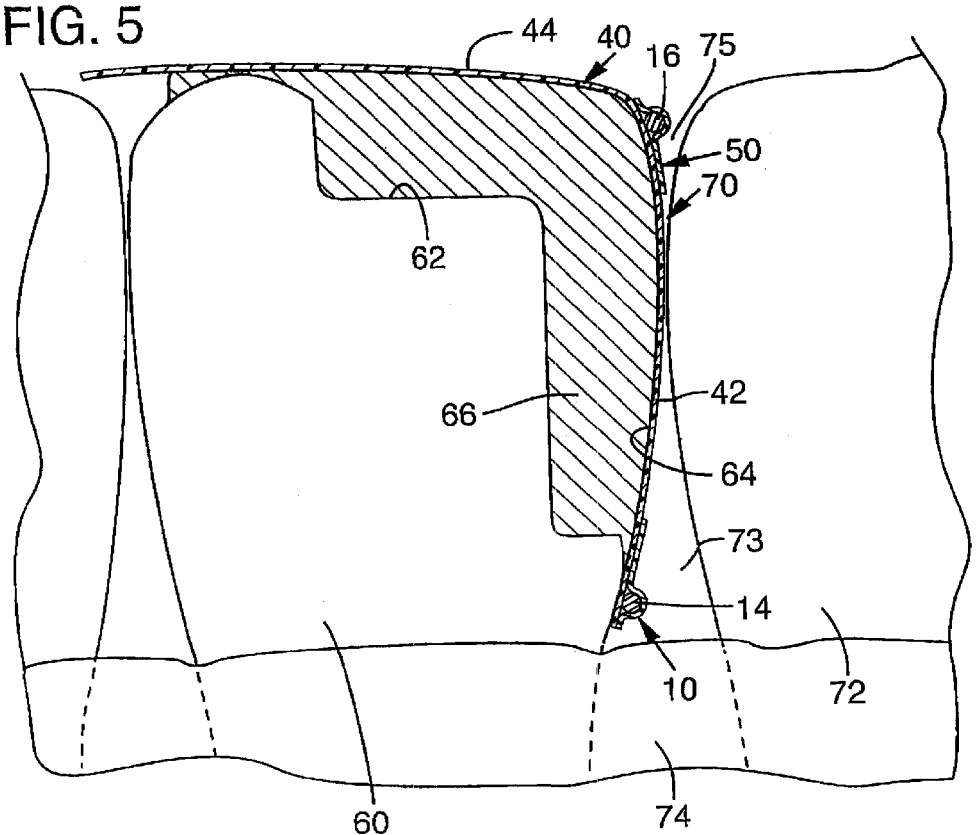
FIG. 5 illustrates the embodiment of FIG. 1 in position relative to a tooth which has been filled with tooth filling material and with the occlusal extension positioned over the biting surface of the tooth.

With reference to FIGS. 1–5, a first embodiment for shaping dental filling material placed in a cavity preparation of a tooth is illustrated.

The illustrated embodiment includes a frame 10 which is shaped to define a frame opening 12. The frame opening is preferably substantially bounded by the frame and desirably entirely enclosed by the frame. The illustrated form of frame 10 shown in FIG. 1 is formed from elongated wire which is bent in a generally rectangular shape. The frame 10 in this form has a gingival side portion 14 and an occlusal side portion 16 which is opposed to and spaced from gingival side portion 14. In addition, the illustrated frame 10 includes first and second frame end portions 18, which extend between the respective ends of side portions 14, 16. The frame 10 may be formed by bending a single wire in the shape of the frame. Also, first and second end portions 22, 24 of the wire may project outwardly from the loop or frame opening formed by the wire, such as outwardly from the corner of the frame opening where frame portions 14, 20 approach one another. A mechanism may be provided for detachably interconnecting the wires 22, 24. In one example, the wire ends 22, 24 may simply be twisted together. Alternatively, a wire end entrapment device may be used. In one form tube or sleeve 26 may be positioned to at least partially surround the wire ends 22, 24. In a typical case the sleeve is elongated and of sufficient length to capture the free ends of these wires. The sleeve 26 may be of a heat shrinkable polymer material which is heated, as explained below, to capture and detachably hold the wire ends 22, 24 together.

The frame 10 may be cut or otherwise separated to facilitate removal of the device as explained below. For example, the sleeve 26 may be made so as to slide free of the wire ends when the tube is pulled toward the distal ends of the wire ends to facilitate their detachment. The wire ends 22, 24 may readily be separated following the removal of the sleeve. When the sleeve is detached, the wire forming the gingival side portion 14 of the frame may be pulled laterally outwardly through the gap at the base of adjacent teeth without having to be pulled upwardly between the proximal surfaces of adjacent teeth during removal of the apparatus.

The illustrated wire frame 10 is generally rectangular in shape, although the frame may assume other shapes. In addition. the gingival border 14 may have a slight concavity or upward arch in order to better fit over the gingival tissues. The frame 10 may also define more than the frame opening, for example side-by-side openings.

The illustrated frame 10, as one specific example, is composed of multi-stranded stainless steel wire with a diameter of 0.014 inch. In this exemplary case, the wire contains 49 strands, 7 strands of 7-stranded wire made by American Fishing Wire of West Chester, Pa. A frame which has such a small diameter where it crosses the occlusal surface between two teeth is advantageous. That is, a frame which does not interfere at all with the full bite is desirable if an acceptable occlusal surface is to be produced by having the patient bite down fully before removal of the frame. Other frame forming materials may also be used.

Again, the two ends 22, 24 of the illustrated wire frame 10 are attached together along their overlap by a sleeve 26. The sleeve 26, as explained above, may be of a length of heat-shrink plastic. One specific example is ST-301 polyolefin tubing available from 3M Company of St. Paul, Minn. The sleeve 26 may be heated and shrunk around the two wire ends to fasten them together in a way that allows them to be easily pulled apart by the dentist after the filling is completed. By simply pulling the plastic sleeve off the wire ends 22, 24, those two wire ends are disattached and the frame is interrupted.

At least one sheet of polymer material is supported by the frame 10 so as to span the frame opening. Most preferably the polymer sheet spans the entire frame opening 12 and is supported along the entire periphery of the frame. The film may be of a light transmissive material so as to permit the passage of light through the film to cure conventional light curable tooth filling materials which are commonly used in dentistry today. By light transmissive it is meant that the material, when illuminated, allows passage of sufficient light to cure the filling material. Most preferably the material is of a clear plastic such as of a polyethylene film having a thickness of from about 0.0003 inch to about 0.0006 inch. Heretofore no one has expected that films that are this thin could be used in shaping filling material along the sides of a tooth being filled. The framework supporting the film adds sufficient strength to minimize the possibility of the film tearing.

In the embodiment of FIG. 1, at least one sheet of such polymer material is used and attached to the frame. For example, a rectangular sheet 40 as shown in FIG. 2 may be secured to the frame so as to entirely span the frame opening 12. Thus, sheet 40 includes a frame opening spanning section 42. In addition, sheet 40 includes an optional occlusal extension section 44, which is thus of one piece construction with section 42 although it may be a separate piece. Occlusal extension section 44 may be positioned over the biting surface of a tooth that has been filled with filling material. The patient may then bite against the section 44 to facilitate the formation of the desired biting surface of the tooth being filled. The section 44 prevents the uncured composite from sticking to the tooth which impacts the section 44 during biting. In the illustrated embodiment, although occlusal section 44 may be supported, it is preferably unsupported about its periphery except where section 44 engages the occlusal side portion 16 of the frame 10.

In addition, the embodiment of FIG. 1 includes a second sheet of polymer material indicated at 50 in FIG. 3. The second sheet of material, which is typically of the same material as the first sheet, although it may differ, has an opening 52 formed therein. The opening is bounded in this case on all sides by an interior edge 54 of the sheet 50. The sheet 50 also has an exterior edge 56. Although not required, in this embodiment sheet 50 continuously and entirely surrounds the opening 52. Opening 52 is preferably sized to have an area which is greater than one-half of (a majority of) the frame opening 12 and more specifically at least about 80 percent of the frame opening area. The size and shape of opening 52 may be varied.

As best seen in FIG. 4, sheet 50 overlays the frame 10 and sheet 40 underlies the frame. Thus, the frame is sandwiched between sheets 40 and 50 in this example. The sheets may be heat-sealed or otherwise affixed to frame 10. In addition, the respective portions of sheet 50 along interior and exterior edges 54, 56 may be sealed to sheet 40 although they may be loose.

The large centrally located hole 52 in sheet 50 allows the total thickness in the middle of the frame opening 12 to be the thickness of a single sheet of material, namely the thickness of sheet 40. The thickness of sheet 40 may be extremely thin ranging from 0.0003 inch to 0.0006 inch with 0.0005 inch being a specifically preferred example. Limiting the thickness of material in the area where the proximal surfaces of adjacent teeth will contact to this extent ensures that the gap which is left between the proximal surfaces of adjacent teeth after the filling is complete and the apparatus removed is non-existent or at most so small that compaction of food in the gap between the teeth during chewing is minimized. Thus, supporting polymer material having a thickness of no greater than 0.0006 inch in the area where the proximal surfaces of the teeth will contact or be closest to one another following the completion of the filling is a desirable aspect of an embodiment of the present invention.

In one specific manufacturing approach, the frame 10 may be heated with the sheets 40, 50 then being pressed against the heated frame to heat-seal the layers to the frame. Heat may also be applied to the sheet 40 after it is secured to the frame to cause the sheet to shrink and tighten the sheet on the frame.

FIG. 5 illustrates a tooth 60 which has been drilled or otherwise prepared by removing decayed material to form a void in the tooth which is bounded in part by a tooth surface 62. Frame sections 14, 16 are shown in FIG. 5 to be of multi-stranded wire. In FIG. 5, a major surface 64 of sheet section 42 is positioned against composite resin or other material 66 placed in the tooth void. As shown in FIG. 5, only a single thickness of the sheet 42 is located in the gap 70 between the tooth 60 and an adjoining tooth 72. Also, the frame side portion 14 is shown positioned at the base of the teeth 60, 72 and in the gap 73 between teeth 60, 72, The gap 73 is along the gingiva 74 which surrounds the teeth. In addition, the frame side portion 16 is in the gap 75 between teeth 60, 72 and adjacent to the occlusal or biting surfaces of these teeth. As can be seen in FIG. 5, the occlusal extension section 44 has been folded or rolled onto the biting surface of the tooth 60. A patient may bite down on section 44 to form an impression in the biting surface of tooth 60 which has the desired contour for mating with the opposing tooth during biting. The resin 66 may then be cured, such as by shining light through films 40, 50, in the case of a light curable resin filling material 66.

Following curing of the filling, the frame 10 may be severed. For example, the sleeve 26 may be removed to free the wires 22, 24 (FIG. 1) from one another. This permits removal of gingival section 14 of the frame without requiring frame section 14 to be pulled upwardly through the gap 70 between teeth 60, 72.

In the event the embodiment of FIG. 1 includes more than one frame opening, typically each frame opening is positioned against a section of the tooth to be filled by the filling material. The procedure as explained above may then be followed.

While heat sealing or heat welding is the preferred way of attaching the film to the frame, it is understood that there are also other suitable ways of attaching a thin plastic film to a wire or other frame, such as dip molding, extrusion or by using adhesive. The invention is not restricted to any specific film or sheet material to frame forming or mounting approach.

One specifically suitable film for sheets 50, 52 is a polyethylene film sold under the brand name Handi-wrap by S.C. Johnson and Son, Inc., of Racine, Wis. This film is about 0.0005 inch thick. While other plastics such as polyester, polyurethane, or polyolefin may be used, polyethylene is preferable for several reasons.

Preferably, a material such as polyethylene which has dead soft quality is selected. Such a material is extremely pliable without memory. The newer composite resins used in fillings are specially designed to have the same dead soft quality so that they can be shaped with a stroke of an instrument and then will not slump or undergo any other changes in form unless further manipulated. When these new composite filling materials are used together with a polyethylene or other dead soft film, it becomes easy to shape the final contours as needed using a simple hand instrument before curing, for example with light.

It is also desirable to select a material like polyethylene which is slightly stretchable. When placed under pressure, such a film stretches in a way that tends to cause the central section of the film between the frame elements to extend or pouch out and form a gradual curve that gives it a contour much like the side of a natural tooth. Such contours which reproduce natural tooth contours are highly desirable.

Figure 6:
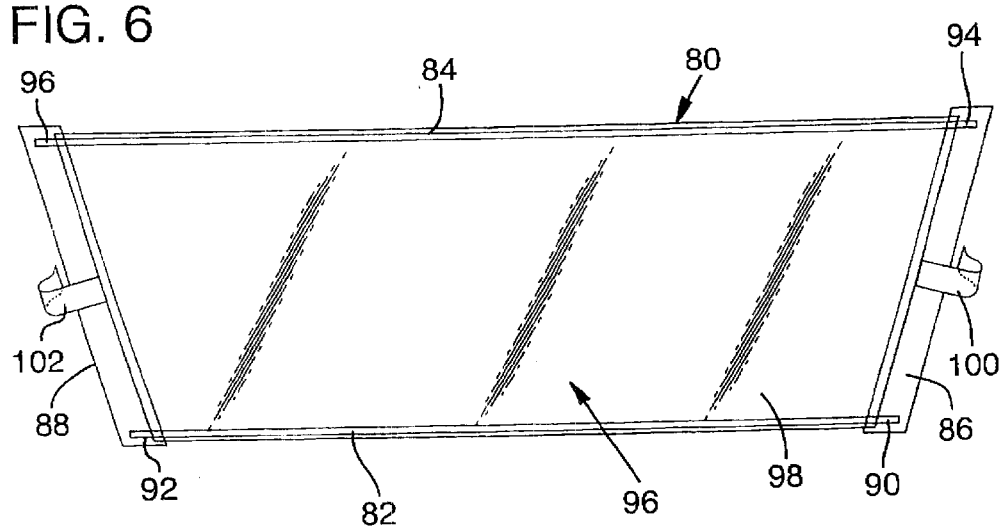
FIG. 6 illustrates an alternative embodiment of a tooth filling material shaping apparatus.

An alternative embodiment for shaping dental filling material placed in a cavity preparation of a tooth is shown in FIG. 6.

In FIG. 6, the frame is indicated at 80 and is of a multi-piece construction. More specifically, the frame 80 in FIG. 6 includes a gingival side portion 82 and an occlusal side portion 84 which is parallel to, spaced from and opposed to the gingival side portion. Frame portions 82, 84 may be, for example, formed of wire such as used in the embodiment of FIG. 1. The illustrated frame 80 also includes first and second spaced apart end portions 86, 88 which extend between the respective ends 90, 92 and 94, 96 of frame sections 82, 84. Frame sections 86, 88 may be made of any suitable material such as is the case for frame sections 82, 84. However, one specific example is to make sections 86, 88 out of sheet material. For example, sections 86, 88 may be stamped, etched or otherwise formed from stainless steel such as from stainless steel sheet material which is 0.002 inch thick. The thickness of elements 86, 88 may be varied.

In the form shown in FIG. 6, the gingival side portion 82 of frame 80 is shorter than the occlusal side portion 84. Consequently, the illustrated frame 80 assumes an inverted trapezoidal shape as shown in FIG. 6. The corresponding elements 14, 16 of the embodiment of FIG. 1 may have similar relative dimensions. The end portions 90, 92 of frame element 82 are secured respectively to frame elements 86, 88. In addition, the end portions 94, 96 of frame element 84 are secured respectively to the frame elements 86, 88. For example, elements 82, 84 may be connected to elements 86, 88 by spot welding or in any other suitable manner. The frame 80 defines a frame opening 96 which, in this case, is spanned by a sheet of material 98 which is preferably the same material as used for the sheet 40 as explained above. Sheet 98 may be heat-sealed or otherwise formed with or secured to the respective frame elements. In one specific manufacturing approach, sheet 98 may be coextruded with elements 80, 82, cut to the desired length, and then secured to the frame elements 86, 88. Following co-extruding and severing of the wires 82, 84, the film 98 may be stamped or otherwise removed where it is not needed prior to spot welding or otherwise securing the occlusal and gingival frame elements 82, 84 to the frame end pieces 86, 88 The embodiment of FIG. 6 also includes a mechanism for attaching the apparatus to the tooth to be filled. For example, first and second adhesive tabs 100, 102 mounted to the respective frame end portions 86, 88 may be provided and attached to a tooth, such as to tooth 100 as shown in FIG. 7. Tooth has a cavity preparation indicated at 112 which has yet to be filled with the filling material. Adhesives and adhesive strips which stick to dried teeth are commonly known. The tabs 100, 102 may be folded against one another, such as indicated generally in FIG. 6, prior to their use in securing the apparatus to a tooth.

As can be seen in FIG. 7, by providing a frame of an inverted trapezoidal shape with the occlusal frame section being slightly longer than the gingival frame section, a degree of taper is provided when the apparatus is wrapped around a tooth as shown in FIG. 7. As a result, the device of this configuration enhances the contouring of the tooth filling.

Figure 9:
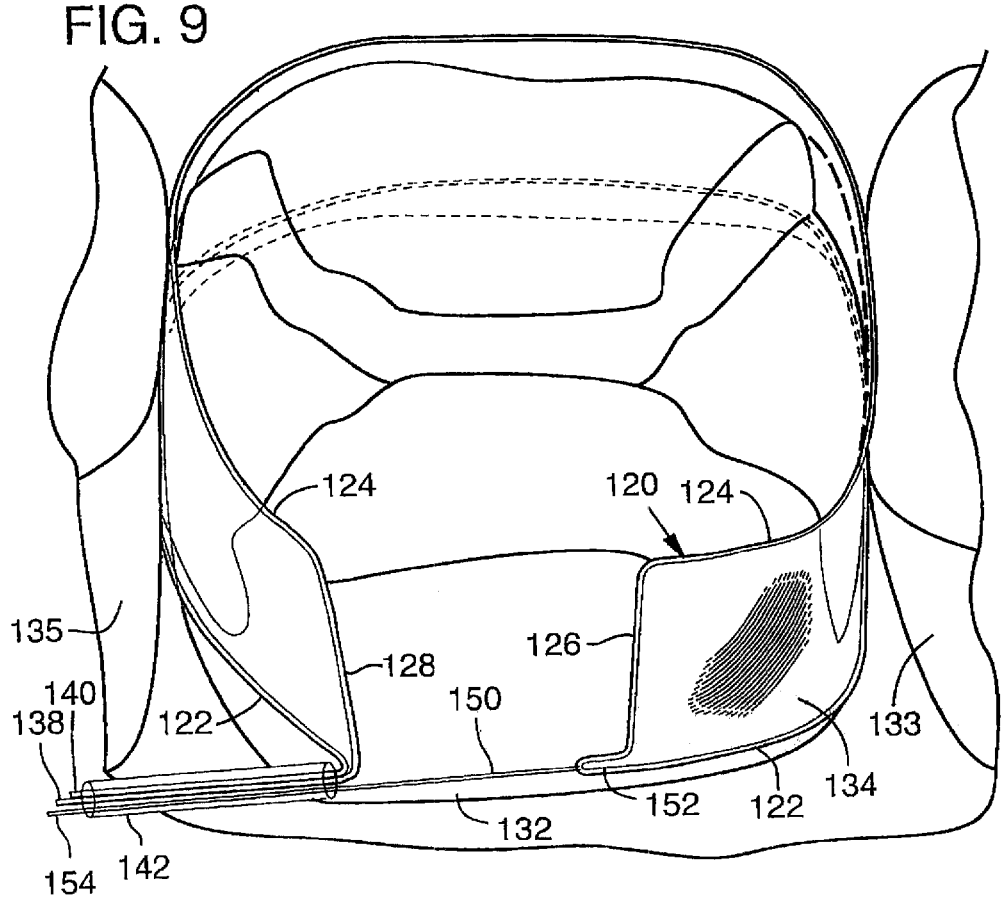
FIG. 9 illustrates the embodiment of FIG. 8 shown in position against a tooth to be filled.

FIG. 8 illustrates another embodiment of an apparatus for shaping dental filling material placed in a tooth cavity preparation. In the embodiment of FIG. 8, a frame 120 is shown. The frame may be constructed of any suitable flexible material to facilitate bending of the frame around the tooth and may, for example, be of the same material as the wire frame described above in connection with the embodiment of FIG. 1. The frame 120 includes a gingival side portion 122 and an occlusal side portion 124 which is opposed to and spaced from the gingival side portion. In addition, frame includes first and second frame end portions 126, 128 extending between the respective gingival and occlusal side portions 122, 124. The frame 120 thus defines a frame opening 130 which is elongated in comparison to the frame opening 12 of FIG. 1 and, for example, as shown in FIG. 9, may substantially surround a tooth 132 being treated. In FIG. 9, the frame 120 passes between the proximal surfaces of teeth 132, 133 and of teeth 132, 135. A sheet 134 is supported by the frame. In the illustrated embodiment, the sheet 134 spans the entire frame opening 120. Sheet 134 may be of a polymer material and may be the same material as used for the sheet 40 in the FIG. 1 embodiment. The sheet 134 may be heat-sealed or otherwise secured to the frame. In the embodiment of FIG. 8, although it may be included, an occlusal extension section has been omitted.

As in the example of FIG. 1, the frame 120 may be formed of a single wire having first and second ends 138, 140 which project outwardly from a frame opening defining loop formed by the wire. A sleeve 142 may capture the ends 138, 140 of the wire and may be heat shrunk to detachably secure the wire ends together as previously explained. The sleeve 142 forms a convenient handle for use by a dentist in gripping the apparatus.

In addition, the embodiment of FIG. 8 includes a mechanism for applying tension to the frame when bent around a tooth. Although this mechanism may take other forms, in the illustrated embodiment, engagement mechanisms are included in the frame 120 for engagement by at least one biasing or tension-applying element, such as a tie 150. In the form shown in FIG. 8, the wire forming the frame 120 includes a loop 152 formed adjacent to the intersection of frame end portion 128 and the gingival side portion 122 of the frame. Tie 150 is tied or otherwise secured to the loop 152. The tie 150 may be attached to the frame 120, for example at the intersection of frame end portion element 128 and the gingival frame section 122. This intersection may be configured to define a hook or other tie engagement element. Alternatively, the sleeve 142 may comprise a form of tie engagement element. In this case, the tie 150 is threaded through sleeve 142. The sleeve 142 may be heat-shrunk in a manner that permits the tie to slide through sleeve 142 upon applying tension to a free end 154 of the tie which projects outwardly from sleeve 142. Consequently, when free end 154 is pulled, the sleeve 142 frictionally retains the tie in place and thereby maintains the tension applied by the tie to the frame. The tie 150 need not pass through a tube as it may simply be tied or otherwise secured. The tie 150 may be of an elastic material such an elastic thread. An elastic thread or cord, having a one-thirty second diameter when unstretched, a braided cover and what appears to be a rubber core from Rhode Island Textile Company of Providence, Rhode Island is a specific example. As a result, an elastic contraction force is continuously applied to the frame. With this construction, the dentist may easily apply the appropriate tension to the frame. In the embodiment shown in FIG. 8, friction between the sleeve and tie 150, as well as a stop (not shown) which may be formed by the wire ends in the event the wire ends terminate within the sleeve, prevents the tie 150 from sliding back through the sleeve after having been pulled to tighten the apparatus around a tooth. By applying tension only to the gingival edge portion of the frame, a tight fit is obtained between the gingival frame portion and the tooth to improve the contour of the filling relative to the contour of the tooth at this location. However, it should be understood that a tension application mechanism may be used to apply tension to other locations, such as to the occlusal border of the frame. As shown in dashed lines in FIG. 8, a second tie 160, which may also be of an elastic material like tie 150, may be provided for this purpose. Tie 160 is passed through loops 162, 164 formed in the frame at the intersection between frame elements 124, 126 and 124, 128. Tie 160 may be threaded through these elements and tied as indicated by the knot 164 in FIG. 8. In the embodiment shown in FIG. 8, with ties 150 and 160 included, tightening of the apparatus along the occlusal and gingival borders may be accomplished independently. Tightening mechanisms such as shown in FIG. 8 may be incorporated into other forms of matrix bands with or without polymer supported by a frame.

Other mechanisms may also be used to apply tension to the frame when wrapped around the tooth. Most preferably these mechanisms provide a continuous elastic traction when in place. For example, a latex strap may be used, especially in completing tooth fillings which involve only a single proximal tooth surface. In such a case the strap may easily be forced between intact tooth contact surfaces on the uninvolved proximal surface of the tooth being treated.

FIG. 9 illustrates the apparatus of FIG. 8 in position around a tooth with the tie 150 tightened. It will be appreciated in FIG. 9 that sleeve 142 will snugly engage the wires 140, 142 and tie 150 following shrinking of the sleeve.

Figure 10:
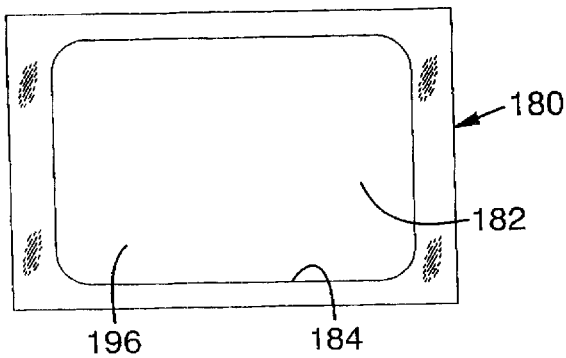
FIGS. 10 and 11 illustrate alternative embodiments of a tooth filling shaping apparatus.
Figure 11:
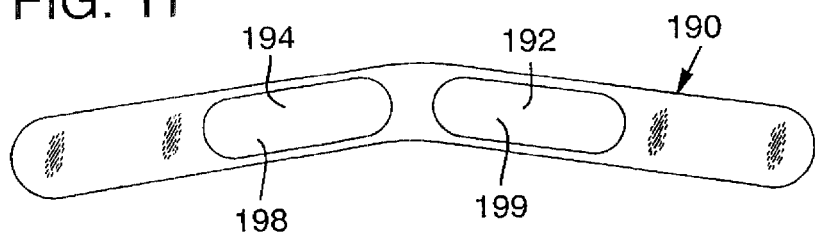

FIG. 10 illustrates an alternative form of frame 180 having an opening 182 therethrough bounded by an interior frame edge 184. The frame 180 may be of one piece construction. For example, frame 180 may be stamped or otherwise formed from sheet material such as stainless steel with 0.002 inch thick stainless steel sheet stock being a specific example. Opening 182 may also be formed in alternative manners, such as by chemically etching the sheet stock to form the frame and also using chemical etching to separate one frame element from similar frame elements located on a sheet. The frame 190 shown in FIG. 11 may be formed in the same manner as the frame of FIG. 10. In the form shown in FIG. 11, first and second frame openings 192, 194 are formed in the material used to form the frame. The openings 182, 192, 194 may be covered by respective sheets of polymer material such as indicated at 196, 198, and 199 in these figures. The material 196, 198, 199 is preferably the same material as used in the FIG. 1 form of the invention. Thus, this material preferably comprises a polymer having a thickness of 0.0003 inch to 0.0006 inch with polyethylene being a preferred polymer. The sheet material 196, 198, 199 may be mounted to frame elements 180, 190 in any convenient manner, such as by heat-sealing or adhesive. Mechanisms for tightening the embodiments of FIG. 10 and FIG. 11 around the tooth may be included. For example, the FIG. 10 embodiment may utilized a mechanism such as shown in FIG. 8. Although less preferred, a conventional matrix tightening mechanism such as a Tofflemire mechanism may be used to tighten the embodiment of FIG. 11.

Having illustrated and described the principles of our invention with reference to a number of preferred embodiments, it should be apparent to those of ordinary skill in the art that the invention may be modified in arrangement and detail without departing from the principles of our invention. For example, the apparatus may be sized to wrap at least partially around more than one tooth, but in this case the apparatus would still wrap at least partially around the one tooth. We claim all such embodiments and modifications which fall within the scope of the following claims.

We claim:

1. An apparatus for shaping dental filling material placed in a cavity preparation of a tooth comprising:

a flexible frame which defines at least one frame opening within the frame;

at least one sheet of polymer material mounted to the frame and spanning the frame opening;

wherein the frame may be wrapped at least partially around a tooth to be filled with at least a portion of the sheet spanning the frame opening being in position to shape the tooth filling material; and wherein the frame has a gingival side portion for positioning adjacent to the gingiva of the tooth when the frame is wrapped at least partially around the tooth to be filled, the frame also having an occlusal side portion opposed to and spaced from the gingival side portion, and wherein the at least one sheet of polymer material includes an occlusal extension portion which may be folded over the biting surface of the tooth.

2. An apparatus according to claim 1 wherein the occlusal extension portion is of a light transmissive polyethelyne material.

3. An apparatus according to claim 2 wherein the occlusal extension portion and said at least one sheet which spans the frame opening are of a common piece of sheet material.

4. An apparatus according to claim 1 wherein the polymer material has a thickness of no greater than 0.0006 inch.

5. An apparatus for shaping dental filling material placed in a cavity preparation of a tooth comprising:

a flexible frame which defines at least one frame opening within the frame;

at least one sheet of polymer material mounted to the frame and spanning the frame opening, the sheet of material having a thickness of from 0.0003 inch to 0.0006 inch;

wherein the frame way be wrapped at least partially around a tooth to be filled with at least a portion of the sheet spanning the frame opening being in position to shape the tooth filling material; and in which said at least one sheet of polymer material comprises first and second sheets of polymer material which sandwich the frame therebetween and which are mounted to the frame, wherein the first sheet entirely spans the frame opening, and wherein the second sheet includes an opening positioned in the region of the frame opening and sized to be of an area which is equal to at least a majority of the area of the frame opening such that a major portion of the frame opening is entirely spanned by a single thickness of the first sheet of polymer sheet material.

6. An apparatus according to claim 5 wherein the frame includes a gingival side portion and an opposed occusal side portion, the first sheet extending beyond the occusal side portion to form a bite surface cover sheet.

7. An apparatus according to claim 6 wherein the first sheet is of a light transmissive material.

8. An apparatus according to claim 7 wherein each of the first and second sheets are of a polyethylene material having a thickness between 0.0003 inch and 0.0006 inch.

9. An apparatus for shaping dental filling material placed in a cavity preparation of a tooth comprising:
- a flexible frame which defines at least one frame opening within the frame;
- at least one sheet of polymer material mounted to the frame and spanning the frame opening, the sheet of material having a thickness of from 0.0003 inch to 0.0006 inch;
- wherein the frame may be wrapped at least partially around a tooth to be filled with at least a portion of the sheet spanning the frame opening being in position to shape the tooth filling material;
- wherein the frame has a gingival side portion and a spaced apart opposed occlusal side portion, the gingival side portion being shorter than the occlusal side portion; and
- wherein the frame is formed of a wire which defines at least one loop which bounds the at least one frame opening.

10. An apparatus according to claim 9 wherein the wire includes first and second end portions which project outwardly from the loop with the first and second end portions being adjacent to one another, and wherein the first and second end portions are detachably interconnected.

11. An apparatus according to claim 10 which includes a wire end portion entrapper which engages at least a portion of the first and second end portions and which detachably interconnects the first and second end portions.

12. An apparatus according to claim 11 in which the wire end portion entrapper comprises a sleeve which surrounds at least a portion of the first and second end portions and which is heat shrunk to detachably interconnect the first and second end portions.

13. An apparatus for shaping dental filling material placed in a cavity preparation of a tooth comprising:
- a flexible frame which defines at least one frame opening within the frame;
- at least one sheet of polymer material mounted to the frame and spanning the frame opening, the sheet of material having a thickness of from 0.0003 inch to 0.0006 inch;
- wherein the frame may be wrapped at least partially around a tooth to be filled with at least a portion of the sheet spanning the frame opening being in position to shape the tooth filling material; and
- in which the frame includes a gingival side portion, an opposed occlusal side portion, and first and second spaced apart frame and portions respectively extending between the gingival and occlusal side portions, the apparatus including at least one tie extending generally from the first frame and portion to the second frame and portion for wrapping around a portion of the tooth opposite to the frame opening and for pulling the frame and portions toward each other and around the tooth to be filled.

14. An apparatus according to claim 13 Wherein the at least one tie comprises a first tie positioned to extend along the gingiva of the tooth and from the first frame end portion to the second frame end portion.

15. An apparatus according to claim 14 in which the first tie is of elastic material.

16. An apparatus according to claim 13 in which the frame is formed of wire in the shape of at least one loop, the wire having first and second wire end portions extending outwardly from the loop, a sleeve at least partially surrounding the first and second wire end portions, and wherein the tie extends through the sleeve.

17. An apparatus according to claim 13 wherein the frame is of a wire and wherein the first and second frame end portions each include a tie engaging projection to which the tie is connected.

18. An apparatus according to claim 17 wherein one of the tie engaging projections comprises a tie engaging, loop formed by the wire.

19. An apparatus for shaping dental filling material placed in a cavity preparation of a tooth comprising:
- a flexible frame which defines at least one frame opening within the frame, the frame having a gingival portion, an occlusal portion and first and second side portions which together define the frame-opening, and wherein the first and second side portions are of a greater width than the width of the gingival and occlusal portions;
- at least one sheet of polymer material mounted to the frame and spanning the frame opening, the sheet of material having a thickness of from 0.0003 inch to 0.0006 inch;
- wherein the frame way be wrapped at least partially around a tooth to be filled with at least a portion of the sheet spanning the frame opening being in position to shape the tooth filling material; and
- wherein the at least one sheet of polymer material spanning the frame opening is of light transmissive material and wherein the tooth filling material is a material which is curable by the application of light, and wherein light may be shined through the sheet and frame opening to cure the tooth filling material; and
- in which the frame is formed of a multistranded wire.

20. A method of making an apparatus for shaping dental filling material placed in cavity preparation of a tooth to be filled, the method comprising;
- forming a flexible frame having at least one frame opening;
- spanning the at least one frame opening with a sheet of polymer film having a thickness which is no greater than 0.0006 inch;
- securing the film to the frame with at least a portion of the frame positioned between at least two layers of polymer material and such that at least the major portion of the frame opening is spanned by only a single thickness of the film.

21. A method of making an apparatus for shaping dental filling material placed in cavity preparation of a tooth to be filled, the method comprising;
- forming a flexible frame having at least one frame opening;
- spanning the at least one frame opening with a sheet of polymer film having a thickness which is no greater than 0.0006 inch;
- securing the film to the frame such that at least the major portion of the frame opening is spanned by only a single thickness of the film; and
- in which the act of forming a flexible frame comprises bending a wire to define the at least one frame opening.

* * * * *

UNITED STATES PATENT AND TRADEMARK OFFICE
CERTIFICATE OF CORRECTION

PATENT NO. : 6,482,005 B1 Page 1 of 1
DATED : November 19, 2002
INVENTOR(S) : Summer et al.

It is certified that error appears in the above-identified patent and that said Letters Patent is hereby corrected as shown below:

Column 4,
Line 22, "18," should be -- 18,20 --.

Column 7,
Line 66, "100" should be -- 110 --.
Line 67, "Tooth has" should be -- Tooth 110 has --.

Column 12,
Line 30, "way" should be -- may --.

Signed and Sealed this

Twenty-third Day of December, 2003

JAMES E. ROGAN
*Director of the United States Patent and Trademark Office*